United States Patent [19]

Wada et al.

[11] Patent Number: 5,079,372

[45] Date of Patent: * Jan. 7, 1992

[54] METHOD FOR PRODUCING A LACTONE

[75] Inventors: Keisuke Wada, Yokohama; Yoshinori Hara, Machida; Koushi Sasaki, Kawasaki, all of Japan

[73] Assignee: Mitsubishi Kasei Corporation, Tokyo, Japan

[*] Notice: The portion of the term of this patent subsequent to Jun. 5, 2007 has been disclaimed.

[21] Appl. No.: 517,175

[22] Filed: May 1, 1990

Related U.S. Application Data

[62] Division of Ser. No. 177,363, Apr. 4, 1988, Pat. No. 4,931,573.

[30] Foreign Application Priority Data

Apr. 18, 1987 [JP] Japan .................. 62-95682

[51] Int. Cl.$^5$ .......................... C07D 307/28
[52] U.S. Cl. .................. 549/325; 549/266; 549/272; 549/273; 549/326; 549/328; 502/213
[58] Field of Search .............. 549/266, 272, 273, 325, 549/326, 328; 502/213

[56] References Cited

U.S. PATENT DOCUMENTS

| | | | |
|---|---|---|---|
| 3,312,718 | 4/1967 | Woskow | 549/325 |
| 3,957,827 | 5/1976 | Lyons | 549/325 |
| 3,997,569 | 12/1976 | Powell | 549/273 |
| 4,268,689 | 5/1981 | Knifton | 502/213 |
| 4,415,740 | 11/1983 | Kaufman | 549/325 |
| 4,620,017 | 10/1986 | Drake | 549/325 |
| 4,931,573 | 6/1990 | Wada et al. | 549/325 |

FOREIGN PATENT DOCUMENTS 2195374  8/1987  Japan .................. 549/325

Primary Examiner—Glennon H. Hollrah
Assistant Examiner—Mark W. Russell
Attorney, Agent, or Firm—Oblon, Spivak, McClelland, Maier & Neustadt

[57] ABSTRACT

A method for producing a lactone by hydrogenating a dicarboxylic acid, a dicarboxylic acid anhydride and/or a dicarboxylic acid ester in the presence of a catalyst, wherein the hydrogenation reaction is conducted in the liquid phase in the presence of (1) ruthenium, (2) an organic phosphine and (3) a compound of a metal selected from the group consisting of Groups IVA, VA and IIIB in the Periodic Table.

According to the present invention, for the production of a lactone by hydrogenating a dicarboxylic acid, a dicarboxylic acid anhydride and/or a dicarboxylic ester, the reaction is conducted in a homogeneous liquid phase reaction by using the ruthenium, organic phosphine and compound of a metal selected from the group consisting of Groups IVA, VA and IIIB, of the present invention as the catalyst, whereby the desired lactone product can be obtained at high selectivity under a mild condition as compared with the conventional methods.

7 Claims, No Drawings

METHOD FOR PRODUCING A LACTONE

This is a division, of application Ser. No. 07/177,363, filed on Apr. 4, 1988 now U.S. Pat. No. 4,931,573.

FIELD OF THE INVENTION

The present invention relates to a method for producing a lactone by hydrogenating a dicarboxylic acid, a dicarboxylic acid anhydride and/or a dicarboxylic acid ester.

DISCUSSION OF BACKGROUND

A method for producing a lactone by hydrogenating a dicarboxylic acid, a dicarboxylic acid anhydride and/or a dicarboxylic acid ester, has been studied since long ago, and various catalysts have been found.

For example, many proposals have been made on a process for producing a lactone by a fixed bed or liquid phase or suspension phase hydrogenation reaction system by using e.g. a nickel-type catalyst (e.g. Japanese Examined Patent Publication No. 6947/1968), a cobalt-type catalyst (e.g. Japanese Unexamined Patent Publication No. 95057/1976), a copper-chromium-type catalyst (e.g. Japanese Examined Patent Publication No. 20119/1963) and a copper-zinc-type catalyst (e.g. Japanese Examined Patent Publication No. 14463/1967). On the other hand, it is also known to produce a lactone by conducting the above-mentioned hydrogenation reaction by using a ruthenium catalyst for a homogeneous system. For example, U.S. Pat. No. 3,957,827 discloses a hydrogenation reaction under a condition of from 40 to 400 psi by using a catalyst of $[RuX_n(PR_1R_2R_3)_xL_y]$ type. U.S. Pat. No. 4,485,246 discloses that a hydrogenation reaction by means of a similar catalyst is conducted in the presence of an organic amine.

However, such conventional methods wherein the nickel-type catalyst, the cobalt-type catalyst, the copper-chromium-type catalyst and the copper-zinc-type catalyst was used, all had a problem that it was necessary to employ a severe condition of a few tens atm. or higher. On the other hand, the conventional method wherein a ruthenium catalyst for a homogeneous system was used, had not only a drawback that the catalytic activity was slightly low, but also fatal problems that the catalytically useful life was extremely short, and the reactor was likely to be corroded by the use of halogen, although the method has a feature that the hydrogenation reaction proceeds under a relatively mild condition.

SUMMARY OF THE INVENTION

It is an object of the present invention to overcome the above-mentioned conventional problems and to provide a method for producing a lactone whereby a dicarboxylic acid, a dicarboxylic acid anhydride and/or a dicarboxylic acid ester can be hydrogenated industrially more advantageously than ever.

The present inventors have conducted extensive research to accomplish the above object, and as a result, have found that in a method for producing a lactone by hydrogenating a dicarboxylic acid, a dicarboxylic acid anhydride and/or a dicarboxylic acid ester, if a catalyst comprising (1) ruthenium, (2) an organic phosphine and (3) a compound of a metal selected from the group consisting of Groups IVA, VA and IIIB, is used as the catalyst, not only the catalytic activity for hydrogenation increases, but also the stability in the activity of the catalyst can be improved. The present invention has been accomplished on the basis of this discovery.

DETAILED DESCRIPTION OF THE PREFERRED EMBODIMENTS

Now, the present invention will be described in detail.

The dicarboxylic acid, the dicarboxylic anhydride and/or a dicarboxylic acid ester used as a starting material of the present invention, is a saturated or unsaturated dicarboxylic acid having from 3 to 7 carbon atoms and/or its derivative.

Specific examples of the dicarboxylic acid include succinic acid, fumaric acid, maleic acid, glutaric acid and methylsuccinic acid. The dicarboxylic acid anhydride includes succinic anhydride, maleic anhydride, glutaric anhydride and methylsuccinic anhydride. As the dicarboxylic acid ester, an alkyl ester is preferred, and particularly preferred is a dicarboxylic acid derivative having 4 carbon atoms. For example, dimethyl maleate, diethyl fumarate and di-n-butyl succinate, may be mentioned.

The catalyst used in the method of the present invention is a catalyst comprising (1) ruthenium, (2) an organic phosphine and (3) a compound of a metal selected from the group consisting of Groups IVA, VA and IIIB of the Periodic Table.

Here, the ruthenium may be used in the form of metal ruthenium or a ruthenium compound. As the ruthenium compound, an oxide, hydroxide, inorganic acid salt, organic acid salt or complex compound of ruthenium may be used. Specifically, there may be mentioned ruthenium dioxide, ruthenium tetraoxide, ruthenium dihydroxide, ruthenium chloride, ruthenium bromide, ruthenium iodide, ruthenium nitrate, ruthenium acetate, tris(acetylacetone)ruthenium, sodium hexachlororuthenate, dipotassium tetracarbonylruthenate, pentacarbonylruthenium, cyclopentadienyldicarbonylruthenium, dibromotricarbonylruthenium, chlorotris(triphenylphosphine)hydridoruthenium, bis(tri-n-butylphosphine)tricarbonylruthenium, dodecacarbonyltriruthenium, tetrahydridedecacarbonyltetraruthenium, dicesium octadecacarbonylhexaruthenate, tetraphenylphosphonium undecacarbonylhydridetriruthenate.

Such metal ruthenium or ruthenium compound is used in an amount such that the concentration in the reaction solution will be 0.0001 to 100 mol, preferably from 0.001 to 10 mol, as ruthenium in one liter of the reaction solution.

In the method of the present invention, it is necessary to use the organic phosphine together with the ruthenium. The organic phosphine is considered to contribute to the control of the electron state of ruthenium or to the stabilization of the activity of ruthenium. Specific examples of such an organic phosphine include a trialkylphosphine such as tri-n-butylphosphine or dimethyl-n-octylphosphine, a tricycloalkylphosphine such as tricyclohexylphosphine, a triarylphosphine such as triphenylphosphine, an alkylarylphosphine such as dimethylphenylphosphine, and a polyfunctional phosphine such as 1,2-bis(diphenylphosphino)ethane.

Such as organic phosphine is used in an amount within a range of from 0.1 to 1,000 mol, preferably from 1 to 100 mol, per mol of ruthenium. The organic phosphine may be supplied to the reaction system by itself or in the form of a composite with ruthenium.

By using a compound of a metal selected from the group consisting of Groups IVA, VA and IIIB of the Periodic Table as an additional accelerator for the ruthenium constituting the main catalyst for the hydrogenation reaction of the present invention, it is possible to have the hydrogenation reaction proceeded under a relatively mild condition by utilizing the merits of the ruthenium as the main component, and it is also possible to improve the catalytic activity for hydrogenation and to improve the stability of the activity and the selectivity for the desired product.

The metal selected from the group consisting of Groups IVA, VA and IIIB of the Periodic Table, includes titanium, zirconium and hafnium in Group IVA; vanadium, niobium and tantalum in Group VA; and boron, aluminum, gallium, indium and thallium in Group IIIB. The compound of such a metal includes a carboxylate, a nitrate, a halide, an oxohalide, a sulfate, a hydroxide, a carbonylate, an oxalate, a phosphate, a chromate, a silicate, a cyano compound, an oxide, a metal alkoxide, an acetylacetonate and an organometallic compound. From the viewpoint of its solubility, corrosion property and thermal stability, it is preferably added in the form of its metal alkoxide, acetylacetonate, carboxylate, hydroxide or oxide to the reaction system.

Specific examples of the compound of a metal selected from the group consisting of Groups IVA, VA and IIIB, include a titanium compound such as titanium tetraethoxide, titanium tetraisopropoxide, titanium tetrabutoxide, ammonium titanium oxalate, titanyl acetylacetonate or titanium hydroxide; a zirconium compound such as zirconium acetylacetonate, zirconium carbonate, zirconium naphthenate, zirconium octate, dicyclopentadiene zirconium dimethoxide, dicyclopentadiene zirconium diethoxide, zirconocene, tetrabutoxy zirconium, tetraethoxy zirconium, zirconium oxyacetate, zirconium oxystearate, zirconium phosphate, zirconium oxynitrate, zirconium sulfate or dicyclopentadiene zirconium dicarbonyl; a hafnium compound such as tetramethoxy hafnium, tetraethoxy hafnium, dicyclopentadiene hafnium dicarbonyl, tetrabenzyl hafnium or tetracyclopentadiene hafnium; a vanadium compound such as vanadium acetylacetonate, vanadyl nitrate, vanadyl sulfate, vanadyl acetylacetonate, vanadyl oxalate, ammonium methavanadate or vanadium hexacarbonyl; a niobium compound such as niobium oxide, dicyclopentadienetrihydride niobium, niobium oxide ethoxide, niobium pentamethoxide or niobium pentaisoproxide; a tantalum compound such as tantalum oxide, tantalum pentamethoxide, tantalum pentaisoproxide, cyclopentadienyltetracarbonyl tantalum, biscyclopentadienyltrimethyl tantalum or pentabenzyl tantalum; a boron compound such as trimethoxy boron, triphenoxy boron, boric acid, boron oxide, orthoboric acid, pyroboric acid, metaboric acid, methylboronic acid, phenylboronic acid, diphenylborinic acid, triphenyl boran, tricyclohexyl boran, tetraethyl diboran, dimethyl(dimethylamino) boran, borazine, triethylboroxine, tricyclohexyl boroxine, triphenyl boroxine, sodium tetraphenylborate, ammonium tetraphenylborate or ammonium tetraoxoborate; an aluminum compound such as triethoxy aluminum, tributoxy aluminum, triethyl aluminum, aluminum acetate, aluminum acetylacetonate, aluminum benzoate or aluminum stearate; a gallium compound such as gallium oxide, gallium triisoproxide, gallium isoproxyacetylacetonate, hydroxydimethyl gallium, trimethyl gallium, methoxydimethyl gallium or dimethyl gallium acetate; an indium compound such as indium trimethoxide, indium triisoproxide, triisopropyl indium, trimethyl indium or phenyl indium diacetate; and a thallium compound such as methyloxo thallium, hydroxydimethyl thallium, methanesulfonate dimethyl thallium, trimethyl thallium, thallium hydroxide, thallium carbonate, thallium acetate, methyl thallium diacetate, triethoxy thallium, butoxydimethyl thallium, diethylaminodimethyl thallium or dimethyl thallium acetylacetonate. Such a metal compound is used in an amount within a range of from 0.01 to 1000 mols, preferably from 0.1 to 100 mols, more preferably from 0.5 to 20 mols, per mol of ruthenium in the main catalyst.

By using a conjugate base of an acid having a pKa of less than 2 as an additional accelerator for the ruthenium, it is possible to improve the catalystic activity for hydrogenation and to improve the stability of activity and the selectivity for the desired product.

The conjugate base of an acid having a pKa of less than 2 may be any material so long as it is capable of forming such a conjugate base during the preparation of the catalyst or in the reaction system. It may be supplied in the form of a Bronsted acid having a pKa of less than 2, or a salt of such an acid. Specifically, there may be mentioned Bronsted acids including inorganic acids such as nitric acid, perchloric acid, borofluoric acid, hexafluorophosphoric acid and fluorosulfonic acid, and organic acids such as trichloroacetic acid, dichloroacetic acid, trifluoroacetic acid, methanesulfonic acid, dodecylsulfonic acid, octadecylsulfonic acid, trifluoromethanesulfonic acid, benzenesulfonic acid, p-toluenesulfonic acid and a sulfonated styrene-divinylbenzene copolymer, or alkali metal salts, alkaline earth metal salts, ammonium salts or silver salts of these Bronsted acids.

It may be added in the form of an acid derivative which is capable of forming such a conjugate base in the reaction system. For example, it may be added in the form of an acid halide, an acid anhydride, an ester or an acid amide to the reaction system to obtain similar effects.

Such an acid or base is used in an amount within a range of from 0.01 to 1,000 mol, preferably from 0.1 to 100 mol, relative to ruthenium.

The method of the present invention may be conducted in the absence of a solvent i.e. by using the starting material for the reaction or the reaction product as the solvent. However, it is possible to use a solvent other than the starting material for the reaction or the reaction product. Such a solvent includes an ether such as diethyl ether, anisole, tetrahydrofuran, ethylene glycol dimethyl ether or dioxane; a ketone such as acetone, methyl ethyl ketone or acetophenone; an alcohol such as methanol, ethanol, n-butanol, benzylalcohol, phenol, ethylene glycol or diethylene glycol; a carboxylic acid such as formic acid, acetic acid, propionic acid or toluylic acid; an ester such as methyl acetate, n-butyl acetate or benzyl benzoate; an aromatic hydrocarbon such as benzene, toluene, ethylbenzene or tetralin; an aliphatic hydrocarbon such as n-hexane, n-octane or cyclohexane; a halogenated hydrocarbon such as dichloromethane, trichloroethane or chlorobenzene; a nitro compound such as nitromethane or nitrobenzene; a carboxylic acid amide such as N,N-dimethylformamide, N,N-dimethylacetamide or N-methylpyrrolidone; other amide such as hexamethylphosphoric acid triamide or N,N,N',N'-tetraethylsulfamide; a urea such as N,N'-dimethylimidazolidone or N,N,N,N-tetramethylurea; a sulfone such as dimethylsulfone or tetramethylenesulfone; a sulfoxide such as dimethylsulfoxide or diphenylsulfoxide; a lactone such as γ-butyrolactone or ε- caprolactone; an polyether such as tetraglyme or 18-crown-6; a nitrile such as acetonitrile or benzonitrile; and a carbonate such as dimethylcarbonate or ethylene carbonate.

The hydrogenation reaction of the present invention may be conducted by introducing the starting material for the reaction, the catalyst component and, if necessary, a solvent, into the reactor, and supplying hydrogen thereto. It is preferred to conduct heat-treatment of the catalyst prior to the introduction of the starting material, by introducing the catalyst component, if necessary together with a solvent, into the reactor and heat-treating it under a hydrogen or argon atmosphere, whereby the formation of by-products will be low and the selectivity will be improved. Such heat-treatment is conducted usually at a temperature of from 100° to 300° C., preferably from 150° to 250° C., for at least 0.5 hour. The hydrogen may be the one diluted with a gas inert to the reaction, such as nitrogen or carbon dioxide.

The reaction is conducted usually at a temperature of from 50° to 250° C., preferably from 100° to 200° C. The hydrogen partial pressure in the reaction system is usually from 0.1 to 100 kg/cm$^2$, preferably from 1 to 30 kg/cm$^2$. It is, of course, possible to conduct the reaction at a lower or higher pressure, but such is not advantageous from the industrial point of view.

The reaction may be conducted either in a batch system or in a continuous system. In the case of a batch system, the required reaction time is usually from 1 to 20 hours.

The desired lactone may be recovered from the reaction solution by a usual separation and purification means such as distillation or extraction. Further, the distillation residue may be recycled to the reaction system as a catalyst component.

Now, the present invention will be described in detail with reference to Examples. However, it should be understood that the present invention is by no means restricted to such specific Examples.

EXAMPLE 1

Into a 70 ml SUS microautoclave, 0.0199 g (Ru: 0.05 mmol) of ruthenium acetylacetonate, 0.185 g (0.5 mmol) of trioctylphosphine, 0.031 g (0.13 mmol) of zirconium oxyacetate and 16 ml of tetraglyme were charged, and heat-treated under an argon atmosphere at 200° C. for 2 hours. To the heat-treated catalyst solution, 4.0 g (40 mmol) of succinic anhydride as the starting material for the reaction was charged, and hydrogen gas was introduced under a pressure of 30 atm. The mixture was heated at 200° C. for 2 hours for the reaction.

After the reaction for a predetermined period of time, the autoclave was opened. The reaction product was analyzed by gas chromatography, whereby the conversion of succinic anhydride was 75.5%, and the yield of γ-butyrolactone (hereinafter referred to simply as "GBL") was 71.8%.

EXAMPLES 2 to 14 and COMPARATIVE EXAMPLE 1

The reaction was conducted in the same manner as in Example 1 except that a metal of Group IVA, VA or IIIB in the Periodic Table as identified in Table 1 was used instead of zirconium oxyacetate in Example 1. Further, for the purpose of comparison, the reaction was conducted in the same manner without adding such a specific metal compound. The results are shown in Table 1.

TABLE 1

| | Metal compound | | Formed GBL (mmol) |
|---|---|---|---|
| | Type | Amount (mmol) | |
| Example 2 | Boric acid | 0.50 | 24.1 |
| Example 3 | Zirconium phosphate | 0.22 | 17.7 |
| Example 4 | Ammonium tetraoxoborate | 0.23 | 20.4 |
| Example 5 | Titanyl acetylacetonate | 0.25 | 13.1 |
| Example 6 | Titanium tetraisoproxide | 0.25 | 15.6 |
| Example 7 | Tri-n-octadecyl borate | 0.50 | 15.1 |
| Example 8 | Tricyclohexylboroxine | 0.50 | 22.3 |
| Example 9 | Aluminum triethoxide | 0.25 | 14.8 |
| Example 10 | Aluminum tributoxide | 0.50 | 16.4 |
| Example 11 | Zirconium oxystearate | 0.13 | 20.5 |
| Example 12 | Zirconium acetylacetonate | 0.25 | 18.0 |
| Example 13 | Ammonium zirconium carbonate | 0.25 | 19.8 |
| Example 14 | Vanadium acetylacetonate | 0.13 | 23.9 |
| Comparative Example 1 | Not added | — | 12.0 |

EXAMPLE 15

The reaction was conducted in the same manner as in Example 1 except that 4.72 g (40 mmol) of succinic acid was used instead of succinic anhydride charged as the starting material for the reaction, whereby the conversion of succinic acid was 52.5%, and the yield of GBL was 51.7%.

EXAMPLES 16 to 20

The reaction was conducted in the same manner as in Example 1 except that the solvent as specified in Table 2 was used instead of tetraglyme used as the solvent in Example 1. The results are shown in Table 2.

TABLE 2

| | Solvent (16 ml) | Formed GBL (mmol) |
|---|---|---|
| Example 16 | Dodecylbenzene | 28.0 |
| Example 17 | Sulfolane | 24.4 |
| Example 18 | N-methylpyrrolidone | 21.2 |
| Example 19 | Acetic acid | 18.8 |
| Example 20 | Dimethyl phthalate | 12.8 |

EXAMPLE 21

Into a bubble tower type SUS reactor, 0.0796 g (Ru: 0.2 mmol) of ruthenium acetylacetonate, 0.74 g (2.0 mmol) of trioctylphosphine, 0.242 g (0.92 mmol) of ammonium tetraoxoborate, 20 ml of tetraglyme and, as the starting material for the reaction, 20.0 g (200 mmol) of succinic anhydride, were charged. While supplying hydrogen gas under normal pressure at a rate of 20 NTP liter/hr, the mixture was heated at 200° C. for 2 hours for reaction, whereby, 27.2 mmol of GBL was obtained.

EXAMPLE 22

The reaction was conducted in the same manner as in Example 21 except that 0.044 g (Ru: 0.1 mmol) of ruthenium acetate was used instead of ruthenium acetylacetonate used in Example 21, whereby 16.0 mmol of GBL was obtained.

EXAMPLE 23

The reaction was conducted in the same manner as in Example 21 except that 0.53 g (2.0 mmol) of triphenylphosphine was used instead of trioctylphosphine used in Example 21, and the reaction temperature was changed to 170° C., whereby 12.2 mmol of GBL was obtained.

EXAMPLE 24

The catalyst, the solvent and the starting material for the reaction were the same as in Example 21, and the reaction condition was changed as follows. Namely, while supplying hydrogen gas under a pressure of 10 atm. at a rate of 100 NTP liter/hr, the mixture was heated at 200° C. for 4 hours for the reaction, whereby the conversion of succinic anhydride was 97.8%, and the yield of GBL was 92.4%.

EXAMPLE 25

The reaction was conducted in the same manner as in Example 24 except that 20 ml of γ-butyrolactone was used instead of tetraglyme used in Example 24, whereby the conversion of succinic anhydride was 96.5%, and the yield of GBL was 84.0%.

EXAMPLE 26

Into a 200 ml induction agitation type SUS autoclave, 0.08 g (0.2 mmol) of ruthenium acetylacetonate, 0.74 g (2.0 mmol) of trioctylphosphine, 0.67 g (1.0 mmol) of zirconium oxystearate and 40 ml of tetraethyleneglycol dimethyl ether were charged. The mixture was heat-treated at 200° C. under a hydrogen pressure of 20 kg/cm$^2$ for 2 hours. Then, the hydrogen pressure was raised to 30 kg/cm$^2$, and a solution prepared by dissolving 25% by weight of maleic anhydride in tetraethyleneglycol dimethyl ether, was introduced into the autoclave at an injection rate of 24 ml/hr by a liquid pump. The mixture was reacted at 200° C. for 2 hours. The total amount of maleic anhydride introduced into the autoclave during the reaction, was 14.8 g (151.4 mmol). After completion of the reaction, the raction solution was taken out, and analyzed, whereby the conversion of maleic anhydride was 97.1%, and the selectivity for GBL was 18.6%.

EXAMPLE 27

The reaction was conducted in the same manner as in Example 26 except that an amount of zirconium oxystearate was changed to 2.01 g (3.0 mmol), and 0.33 g (1.76 mmol) of p-toluenesulfonic acid was added. The total amount of maleic anhydride introduced into the autoclave was 12.9 g (132.4 mmol). After completion of the reaction, the analysis was conducted, whereby the conversion of maleic anhydride was 96.7%, and the selectivity for GBL was 35.1%.

EXAMPLES 28 to 30

The reaction was conducted in the same manner as in Example 27 except that a metal compound as identified in Table 3 was used instead of 2.01 g of zirconium oxystearate. The results are shown in Table 3.

EXAMPLE 31

Into a 200 ml induction agitation type SUS autoclave, 0.08 g (0.2 mmol) of ruthenium acetylacetonate, 0.74 g (2.0 mmol) of trioctylphosphine, 0.33 g (1.76 mmol) of p-toluenesulfonic acid, 2.01 g (3.0 mmol) of zirconium oxystearate and 64 ml of tetraethyleneglycol dimethyl ether were charged. The mixture was heat-treated at 200° C. under a hydrogen pressure of 20 kg/cm$^2$ for 2 hours.

The autoclave was cooled and opened under argon atmosphere, and 16 g (160 mmol) of succinic anhydride was added thereto. Then, the reaction was conducted at 200° C. under a hydrogen pressure of 30 kg/cm$^2$ for 2 hours.

After completion of the reaction, the raction solution was taken out, and analyzed, whereby the conversion of succinic anhydride was 74.0%, and the selectivity for GBL was 94.5%.

What is claimed is:

1. A method for producing a lactone, which comprises hydrogenating in the liquid phase a dicarboxylic acid, a dicarboxylic acid anhydride or a dicarboxylic acid ester or a combination thereof, each being saturated or unsaturated and having from 3 to 7 carbon atoms, in the presence of a catalyst, said catalyst comprising (1) ruthenium, (2) an organic phosphine selected from the group consisting of trioctylphosphine, tri-n-butylphosphine, dimethyl-n-octylphosphine, tricyclohexylphosphine, triphenylphosphine, dimethylphenylphosphine and 1,2-bis(diphenylphosphino)ethane and (3) a compound of a metal selected from the group consisting of groups IVA, VA and IIIB of the Periodic Table.

2. A method for producing a lactone, which comprises hydrogenating in the liquid phase a dicarboxylic acid, a dicarboxylic acid anhydride or a dicarboxylic acid ester or a combination thereof, each being saturated or unsaturated and having from 3 to 7 carbon atoms, in the presence of a catalyst, said catalyst comprising (1) ruthenium, (2) an organic phosphine selected from the group consisting of trioctylphosphine, tri-n-butylphosphine, dimethyl-n-octylphosphine, tricyclohexylphosphine, triphenylphosphine, dimethylphenylphosphine and 1,2-bis(diphenylphosphino)ethane, (3) a compound of a metal selected from the group consisting of groups IVA, VA and IIIB of the Periodic Table, and (4) a conjugate base of an acid having a pKa of less than 2.

3. The method according to claim 1, wherein said ruthenium compound is selected from the group consisting of ruthenium dioxide, ruthenium tetroxide, ruthenium dihydroxide, ruthenium chloride, ruthenium bromide, ruthenium iodide, ruthenium nitrate, ruthenium acetate, tris(acetylacetone)ruthenium, sodium hexachlororuthenate, dipotassium tetracarbonylruthe-

TABLE 3

| | Compound of metal | | Amount of maleic anhydride supplied (g) | Reaction results | | | |
|---|---|---|---|---|---|---|---|
| | Name of metal compound | Amount (mmol) | | Conversion of maleic anhydride (%) | Selectivity for the total of GBL and succinic anhydride (%) | Selectivity for propionic acid (%) | Yield of GBL (%) |
| Example 28 | Zirconium chloride | 2.0 | 12.7 | 96.3 | 78.2 | 13.3 | 30.1 |
| Example 29 | Titanium acetylacetonate | 1.0 | 12.8 | 93.6 | 48.1 | 44.2 | 6.5 |
| Example 30 | Vanadium acetylacetonate | 5.0 | 12.7 | 95.1 | 67.2 | 25.3 | 23.2 | nate, pentacarbonylruthenium, cyclopentadienylidicarbonylruthenium, dibromotricarbonylruthenium, chlorotris(triphenylphosphine)hydridoruthenium, bis(tri-n-butylphosphine) tricarbonylruthenium, dodecacarbonyltriruthenium, tetrahydridedecacarbonyltetraruthenium, dicesium octadecacarbonylhexaruthenate and tetraphenylphosphonium undecacarboynylhydridetriruthenate.

4. The method according to claim 1, wherein said metal of group IVA is titanium, zirconium or hafnium, said metal of group VA is vanadium, niobium or tantalum; and said metal of group IIIB is boron, aluminum, gallium, indium or thallium.

5. The method according to claim 1, wherein said hydrogenation is conducted at a temperature of from about 50°-250° C. with a hydrogen partial pressure of from 0.1-100 kg/cm$^2$.

6. The method according to claim 2, wherein said ruthenium is a ruthenium metal or a ruthenium compound selected from the group consisting of ruthenium dioxide, ruthenium tetroxide, ruthenium dihydroxide, ruthenium chloride, ruthenium bromide, ruthenium iodide, ruthenium nitrate, ruthenium acetate, tris-(acetylacetone)ruthenium, sodium hexachlororuthenate, dipotassium tetracarbonylruthenate, pentacarbonylruthenium, cyclopentadienyldicarbonylruthenium, dibromotricarbonylruthenium, chlorotris(triphenylphosphine)hydridoruthenium, bis(tri-n-butylphosphine) tricarbonylruthenium, dodecacarbonyltriruthenium, tetrahydridedecacarbonyltetraruthenium, dicesium octadecacarbonylhexaruthenate and tetraphenylphosphonium undecacarbonylhydridetriruthenate.

7. The method according to claim 2, wherein said metal of group IVA is titanium, zirconium or hafnium, said metal of group VA is vanadium, niobium or tantalum; and said metal of group IIIB is boron, aluminum, gallium, indium or thallium.

* * * * *